US012496415B2

(12) United States Patent
Zinovik et al.

(10) Patent No.: US 12,496,415 B2
(45) **Date of Patent: *Dec. 16, 2025**

(54) NICOTINE POWDER INHALER

(71) Applicant: PHILIP MORRIS PRODUCTS S.A., Neuchâtel (CH)

(72) Inventors: Ihar Nikolaevich Zinovik, Peseux (CH); Gerard Zuber, Froideville (CH)

(73) Assignee: Philip Morris Products S.A., Neuchâtel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/405,458

(22) Filed: Jan. 5, 2024

(65) Prior Publication Data

US 2024/0139442 A1 May 2, 2024

Related U.S. Application Data

(63) Continuation of application No. 17/168,417, filed on Feb. 5, 2021, now Pat. No. 11,878,114, which is a (Continued)

(30) Foreign Application Priority Data

Apr. 28, 2014 (EP) .................................... 14166205

(51) Int. Cl.
*A61M 15/06* (2006.01)
*A24F 42/20* (2020.01)
(Continued)

(52) U.S. Cl.
CPC ............. *A61M 15/06* (2013.01); *A24F 42/20* (2020.01); *A24F 42/60* (2020.01); *A61M 15/0003* (2014.02); *A61M 15/0008* (2014.02); *A61M 15/0028* (2013.01); *A61M 15/003* (2014.02); *A61M 15/0021* (2014.02);
(Continued)

(58) Field of Classification Search
CPC .......... A24F 40/48; A24F 40/40; A24F 40/20; A24F 40/00; A61M 15/003; A61M 15/008; A61M 15/0036
See application file for complete search history.

(56) References Cited

U.S. PATENT DOCUMENTS 4,597,961 A 7/1986 Etscorn
4,655,229 A 4/1987 Sensabaugh, Jr. et al.
(Continued)

FOREIGN PATENT DOCUMENTS

CN 1059649 A 3/1992
CN 1292714 A 4/2001
(Continued)

OTHER PUBLICATIONS

International Search Report and Written Opinion for PCT/IB2015/000924, issued by the European Patent Office as the International Search Authority, Oct. 7, 2015; 9 pgs.
(Continued)

*Primary Examiner* — Alex B Efta
(74) *Attorney, Agent, or Firm* — Mueting Raasch Group

(57) ABSTRACT

This disclosure relates to nicotine powder inhalers where the nicotine powder is delivered at air flow rates that mimic a smoking regime.

16 Claims, 4 Drawing Sheets

Figure 1:
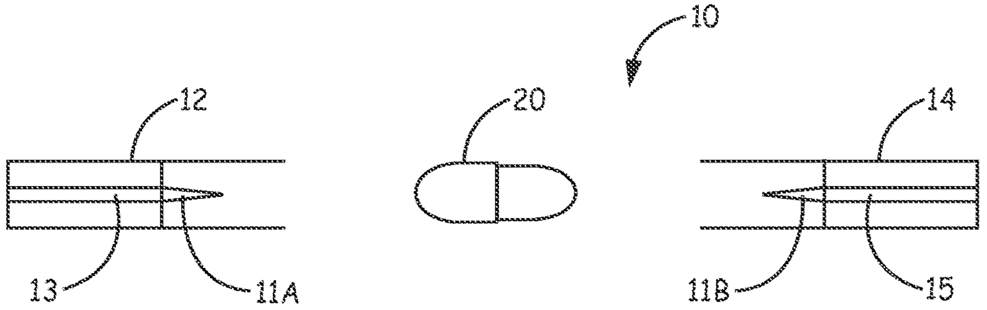

Related U.S. Application Data continuation of application No. 15/124,562, filed as application No. PCT/IB2015/000924 on Apr. 23, 2015, now Pat. No. 10,932,492.

(60) Provisional application No. 61/984,967, filed on Apr. 28, 2014.

(51) Int. Cl.
*A24F 42/60* (2020.01)
*A61M 15/00* (2006.01)

(52) U.S. Cl.
CPC ... *A61M 15/0036* (2014.02); *A61M 2202/064* (2013.01); *A61M 2206/16* (2013.01)

(56) References Cited

U.S. PATENT DOCUMENTS

| | | | |
|---|---|---|---|
| 4,735,217 | A | 4/1988 | Gerth et al. |
| 5,441,060 | A | 8/1995 | Rose et al. |
| 5,746,227 | A | 5/1998 | Rose et al. |
| 6,098,632 | A | 8/2000 | Turner |
| 6,234,169 | B1 * | 5/2001 | Bulbrook .............. A61M 15/06 128/203.15 |
| 7,089,934 | B2 * | 8/2006 | Staniforth ......... A61M 15/0068 128/203.15 |
| 8,256,433 | B2 | 9/2012 | Gonda |
| 8,561,609 | B2 | 10/2013 | Donovon et al. |
| 10,912,334 | B2 * | 2/2021 | Zinovik ............ A61M 15/0028 |
| 10,932,492 | B2 * | 3/2021 | Zinovik ................ A61M 15/06 |
| 11,878,114 | B2 * | 1/2024 | Zinovik .................. A24F 42/20 |
| 2001/0026788 | A1 | 10/2001 | Piskorz |
| 2002/0092520 | A1 | 7/2002 | Casper et al. |
| 2002/0092521 | A1 | 7/2002 | Sullivan et al. |
| 2002/0092524 | A1 | 7/2002 | Lockhart et al. |
| 2004/0204440 | A1 | 10/2004 | Staniforth et al. |
| 2004/0206350 | A1 | 10/2004 | Alston |
| 2005/0022812 | A1 * | 2/2005 | Hrkach ................ A61K 9/0075 128/203.15 |
| 2006/0147389 | A1 * | 7/2006 | Staniforth ......... A61M 15/0028 424/46 |
| 2007/0062548 | A1 | 3/2007 | Horstmann et al. |
| 2007/0221216 | A1 | 9/2007 | Ganem |
| 2008/0241255 | A1 | 10/2008 | Rose et al. |
| 2011/0220106 | A1 | 9/2011 | Ganem et al. |
| 2011/0297166 | A1 | 12/2011 | Takeuchi et al. |
| 2012/0145150 | A1 * | 6/2012 | Donovan ............ A61M 15/001 128/203.15 |
| 2013/0180524 | A1 | 7/2013 | Shahaf et al. |
| 2014/0088044 | A1 | 3/2014 | Rigas et al. |
| 2015/0343159 | A1 * | 12/2015 | Farr .................. A61M 15/0026 128/203.15 |
| 2017/0035107 | A1 | 2/2017 | Zinovik |
| 2017/0035108 | A1 | 2/2017 | Zinovik |
| 2021/0153545 | A1 | 5/2021 | Zinovik |

FOREIGN PATENT DOCUMENTS

| | | | |
|---|---|---|---|
| CN | 2609565 | Y | 4/2004 |
| CN | 1668355 | A | 9/2005 |
| CN | 1805731 | A | 7/2006 |
| CN | 1889861 | A | 1/2007 |
| CN | 103068266 | A | 4/2013 |
| CN | 103566444 | A | 2/2014 |
| EP | 2 399 637 | A1 | 12/2011 |
| EP | 2609822 | A1 | 7/2013 |
| EP | 1509267 | B1 | 1/2015 |
| GB | 2 461 008 | A | 12/2009 |
| GB | 2 497 616 | A | 6/2013 |
| JP | S60192581 | A | 10/1985 |
| JP | 2002522173 | A | 7/2002 |
| WO | WO 91/01656 | A1 | 2/1991 |
| WO | WO 91/18636 | A1 | 12/1991 |
| WO | WO 97/12639 | A1 | 4/1997 |
| WO | WO 99/47196 | A1 | 9/1999 |
| WO | WO 00/09188 | A1 | 2/2000 |
| WO | WO 03/090715 | A2 | 11/2003 |
| WO | WO 2005/049449 | A1 | 6/2005 |
| WO | WO 2010/095659 | A1 | 8/2010 |
| WO | WO 2010/130982 | A2 | 11/2010 |
| WO | WO 2013/128447 | A1 | 9/2013 |

OTHER PUBLICATIONS

Extended European Search Report for EP 14166205.6, issued by the European Patent Office, Oct. 9, 2014; 5 pgs.
International Preliminary Report on Patentability for PCT/IB2015/000924, issued by the International Bureau of WIPO, on Nov. 10, 2016; 6 pgs.
European Communication pursuant to Article 94(3) for EP Application No. 15751065.2-1601, dated Jan. 3, 2018, 5 pgs.
Chinese Office Action for corresponding CN Application No. 201580019505.5, issued by the Chinese Patent Office on Jan. 28, 2019, including English Translation, 20 pgs.
Japanese Office Action, including English Translation, Issued by the Japanese Patent Office on Feb. 21, 2019 for JP 2016-565018, 10 pgs.
Chinese Office Action for Application No. 201580019505.5, issued by the China National Intellectual Property Administration on Aug. 7, 2019; including English Translation: 18 pgs.
Japanese Decision on Rejection issued by the Japanese Patent Office on Sep. 26, 2019 for JP Application No. 2016-565018; 8 pgs. Including English Translation.
Chinese Rejection Decision for CN Application No. 201580019505.5, issued by the China National Intellectual Property Administration on Dec. 2, 2019; 19 pgs. Including English Translation.
Jarvik et al., "Beneficial Effects of Nicotine," *British Journal of Addiction*, May 1991; 86(5):571-575.
Canadian Examination Report for CA 2943459 issued by the Canadian Patent Office on Jan. 7, 2022; 6 pgs.

* cited by examiner

NICOTINE POWDER INHALER

This application is a continuation of U.S. application Ser. No. 17/168,417, filed 5 Feb. 2021, which is a continuation of U.S. application Ser. No. 15/124,562, filed 8 Sep. 2016, which is a § 371 U.S. National Stage of International Application No. PCT/IB2015/000924, filed 23 Apr. 2015, which claims the benefit of U.S. Provisional Application No. 61/984,967, filed 28 Apr. 2014 and EP Application No. 14166205.6, filed 28 Apr. 2014, each of which are incorporated by reference herein.

This disclosure relates to nicotine powder inhalers, where the nicotine powder is delivered at low air flow rates.

Dry powder inhalers (DPI) are known and are used to treat respiratory diseases by delivering a dry powder comprising a pharmaceutical, in aerosol form through inhalation to the patients' airways. For delivery deep into the lungs, particles in the range of 1 to 5 micrometers are required. In pharmaceutical dry powders, the active pharmaceutical ingredient (API) is agglomerated on the surface of larger carrier particles, e.g. lactose, and DPI's therefore operate complex mechanisms to ensure such agglomerates disperse, break up or disaggregate before the API can be inhaled deep into the lungs. Pharmaceutical dry powders containing lactose as a carrier are typically in the range of 20 to 100 micrometers. Existing DPI's for example first "grind" or de-agglomerate the dry powder or impact the larger particles of the dry powder to result in the aforementioned particle size range.

DPI's rely on the force of the patients' inhalation to entrain the powder from the device to subsequently break-up the powder into particles that are small enough to enter the lungs. Sufficiently high inhalation rates are required to ascertain correct dosing and complete disaggregation of the powder. Typically a large amount of API remains attached on the surface of the carrier and is deposited in the upper airways due to incomplete de-aggregation of the powder. Inhalation rates of existing DPI's are usually in the range of 40-120 liters/min (L/min). Existing DPI's are therefore only suitable for delivering dry powders to users in a manner that is different from the inhalation rate associated with smoking articles.

It would be desirable to provide a nicotine powder inhaler that can deliver nicotine powder to a user at inhalation or air flow rates that are close to or within conventional smoking regime inhalation or air flow rates. It would be desirable to provide a nicotine powder inhaler that is a similar size and configuration as a conventional cigarette. It would be desirable to provide a nicotine powder inhaler that can provide a metered dose of nicotine and an optional simultaneous delivery of a second active ingredient.

Nicotine powder inhalers of the invention described herein can be utilized to deliver nicotine to a user at inhalation or air flow rates that are within conventional smoking regime inhalation or air flow rates. The nicotine powder inhalers can provide a predictable and metered dose of nicotine or other optional active ingredients. Nicotine powder inhalers of the invention described herein have a similar size and configuration as a conventional cigarette and have a simple configuration.

As described herein, a nicotine powder inhaler includes a body extending between a mouthpiece and a distal end portion and an airflow channel extends along the body of the inhaler. A nicotine powder receptacle along the airflow channel holds a dose of nicotine powder. The dose of nicotine powder can be inhaled into lungs of a user at an inhalation rate of less than about 5 L/min or preferable less than about 2 L/min. Preferably the dose of nicotine powder can be contained in a capsule that can be pierced by the inhaler. Preferably the dose of nicotine is a nicotine salt.

Various aspects of the nicotine powder inhalers described herein may have one or more advantages relative to standard dry powder inhalers. For example, the nicotine powder inhalers deliver the dry powder nicotine at inhalation or air flow rates that are within conventional smoking regime inhalation or air flow rates and inhalation manner. This allows users with even compromised or impaired breathing conditions to successfully deliver the dry powder nicotine and optional second active ingredients. The nicotine powder inhalers described herein have a simplified configuration that allows the user to predetermine the metered dose of dry powder nicotine and optional second active ingredients. The dry powder nicotine utilized with this inhaler, and described herein, is carrier-free and has a constant size from storage to inhalation. Additional advantages of one or more aspects flavour delivery system described herein will be evident to those of skill in the art upon reading and understanding the present disclosure.

The term "nicotine" refers to nicotine and nicotine derivatives such as nicotine salts.

The present disclosure provides nicotine powder inhalers for inhaling dry powder nicotine. The nicotine powder inhalers include a body extending between a mouthpiece portion and a distal end portion. An airflow channel extends between the mouthpiece portion and a distal end portion and a nicotine powder receptacle. The nicotine powder receptacle is disposed along the airflow channel and is configured to receive a dose of nicotine powder. Surprisingly, the dose of nicotine powder can be inhaled into lungs of a user at an inhalation rate of less than about 5 L/min or less than about 2 L/min which mimics the inhalation flow rate utilized for a conventional smoking regime. The nicotine powder inhalers described herein are "passive" devices that utilize only the inhalation air flow created by the lungs of a user to create air flow though the body of the nicotine powder inhaler.

The airflow path or airflow channel through the body of the inhaler is a simple path or channel. In many embodiments the airflow path or airflow channel through the body of the inhaler is parallel to a longitudinal axis of the inhaler and is linearly extending along an entire length of the inhaler body. In some embodiments the inhaler includes two or three co-extensive airflow channels. One, two or all three of the airflow channels can include a capsule receptacle. In some embodiments the one or more airflow paths or airflow channels includes a swirl generator element that is configured to induce a rotational movement of the airflow moving through the body of the inhaler. The swirl generator element can discharge into an outlet channel that can be a larger volume than the one or more individual airflow paths or airflow channels.

The nicotine powder receptacle can receive a capsule of nicotine powder. The capsule can contain a predetermined amount or dose of nicotine powder. In many embodiments the capsule can contain enough nicotine powder to provide at least 2 inhalations or "puffs" of nicotine powder, or at least about 5 inhalations or "puffs" of nicotine powder, or at least about 10 inhalations or "puffs" of nicotine powder. In many embodiments the capsule can contain enough nicotine powder to provide from about 5 to 50 inhalations or "puffs" of nicotine powder, or from about 10 to 30 inhalations or "puffs" of nicotine powder. Each inhalation or "puff" of nicotine powder can deliver from about 0.5 mg to about 3 mg of nicotine powder to the lungs of the user or from about 1 mg to about 2 mg of nicotine powder to the lungs of the user or about 1 mg of nicotine powder to the lungs of the user.

In many embodiments the capsule holds or contains at least about 5 mg of nicotine powder or at least about 10 mg of nicotine powder. In many embodiments the capsule holds or contains less than about 30 mg of nicotine powder or less than about 25 mg of nicotine powder, or less than 20 mg of nicotine powder. In many embodiments the capsule holds or contains from about 5 mg to about 30 mg of nicotine powder or from about 10 mg to about 20 mg of nicotine powder.

The capsule can be formed of an airtight material that can be pierced or punctured by the inhaler. The capsule can formed of a metallic or polymeric material that serves to keep contaminates out of the capsule but can be pierced or punctured by the inhaler during use.

The inhaler can include a piercing element or pair of opposing piercing elements that are configured to pierce the capsule of nicotine powder. The piercing element or pair of opposing piercing elements fluidly connect the airflow channel with the dose of nicotine powder. The piercing element or pair of opposing piercing elements can engage with the capsule of nicotine powder upon loading the capsule of nicotine powder into the nicotine powder receptacle or upon demand by an actuator on the body of the inhaler.

In many embodiments the nicotine powder is a pharmaceutically acceptable nicotine salt or nicotine salt hydrate. Useful nicotine salts or nicotine salt hydrates include nicotine bitartrate, nicotine salicylate, nicotine fumarate, nicotine mono-pyruvate, nicotine glutamate or nicotine hydrochloride, for example. The compound combining with nicotine to from the salt or salt hydrate can be chosen based on its pharmacological effect. For example: nicotine salicylate can be administered for fever relief, as an anti-inflammatory or painkiller; nicotine fumarate can be administered to treat multiple sclerosis; and nicotine mono-pyruvate can be administered for treating chronic obstructive pulmonary disease (COPD) or for weight loss.

The nicotine powder can have any useful size distribution for inhalation delivery into the lungs of a user. In many embodiments at least about 90 wt % of the nicotine powder has a particle size of about 10 micrometers or less, preferably about 7 micrometers or less. The nicotine powder preferably has a mean average diameter size range from about 0.1 to about 10 micrometers, more preferably from about 1 to about 7 micrometers, even more preferably from about 2 to 6 about micrometers.

Conventional formulations for dry powder inhalation typically contain carrier particles that serve to increase the fluidization of the active particles since the active particles are typically too small to be influenced by the airflow though the inhaler. The carrier particles thus were utilized to improve the dose uniformity by acting as a diluent or bulking agent in a formulation. However, the nicotine powder described herein is carrier-free. Being carrier-free allows the nicotine powder to be inhaled and delivered to the user's lungs at inhalation or airflow rates that are similar to typical smoking regime inhalation or airflow rates. In addition, since the nicotine powder is carrier-free, the airflow path of the inhaler can have simple geometry or a simple configuration.

The carrier-free nicotine powder described herein can be a surface modified nicotine salt where the nicotine salt particle is a coated particle. One preferred coating material is L-leucine.

These carrier-free nicotine powders are described and are available from Telcos Pharma Inc., Espoo, Finland. One particularly useful nicotine powder is an L-luecine coated nicotine bitartrate.

A second active agent or ingredient can be delivered along with the nicotine powder. The second active agent or ingredient can be mixed with the nicotine in the capsule or separate from the nicotine in its own capsule. The second active agent or ingredient can be fluidized with the nicotine powder and inhaled by a user.

This second active agent or ingredient can be any active pharmaceutical material. In many embodiments the second active agent or ingredient can be combined with the nicotine powder described herein by blending the two materials during inhalation. The nicotine powder and the second active agent or ingredient can be blended in the same capsule or provided in series in a single air flow channel in the DPI or provided in parallel in separate flow channels of the DPI. The second active agent or ingredient can have a similar mean average diameter size range as the nicotine powder described above.

The nicotine powder inhaler is less complex and has a simplified powder storage and airflow path as compared to existing DPIs, and does not need a carrier ingredient, such as lactose, as described above. Therefore the complex mechanisms to dissociate/disaggregate a pharmaceutical dry powder is not required in the described nicotine inhaler and therefore the described nicotine inhaler operates under low airflow. The inhaler does not require the typical high inhalation rates of conventional DPIs to deliver the dry nicotine powders described above deep into the lungs.

The nicotine inhaler according to this invention operates using a flow rate of less than about 5 L/min or less than about 3 L/min or less than about 2 L/min or about 1.6 L/min. In many embodiments the flow rate is in a range from about 1 L/min to about 3 L/min or from about 1.5 L/min to about 2.5 L/min. In preferred embodiments the inhalation rate or flow rate is similar to that of Health Canada smoking regime, that is about 1.6 L/min. In contrast, a conventional DPI operates at a flow rate of about 40-120 L/min and often requires an energy source or propellant to promote air flow to achieve this air flow rate.

The nicotine inhaler described herein can be used by a consumer like smoking a conventional cigarette or vaping an electronic cigarette. Such smoking or vaping is characterized by two steps: a first step during which a small volume containing the full amount of nicotine desired by the consumer is drawn into the mouth cavity, followed by a second step during which this small volume comprising the aerosol comprising the desired amount of nicotine is further diluted by fresh air and drawn deeper into the lungs. Both steps are controlled by the consumer. During the first inhalation step the consumer can determine the amount of nicotine to be inhaled. During the second step, the consumer can determine the volume for diluting the first volume to be drawn deeper into the lungs, maximizing the concentration of active agent delivered to the airway epithelial surface. This smoking mechanism is sometimes called "puff-inhale-exhale".

All scientific and technical terms used herein have meanings commonly used in the art unless otherwise specified. The definitions provided herein are to facilitate understanding of certain terms used frequently herein.

The terms "upstream" and "downstream" refer to relative positions of elements of the inhaler described in relation to the direction of inhalation air flow as it is drawn through the body of the inhaler from a distal end portion to the mouthpiece portion.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

FIGS. 1-7 are schematic diagrams of illustrative nicotine powder inhalers 10. FIGS. 3-7 are shown with transparent bodies for ease of illustration of the flow channels and internal elements. The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

Figure 2:
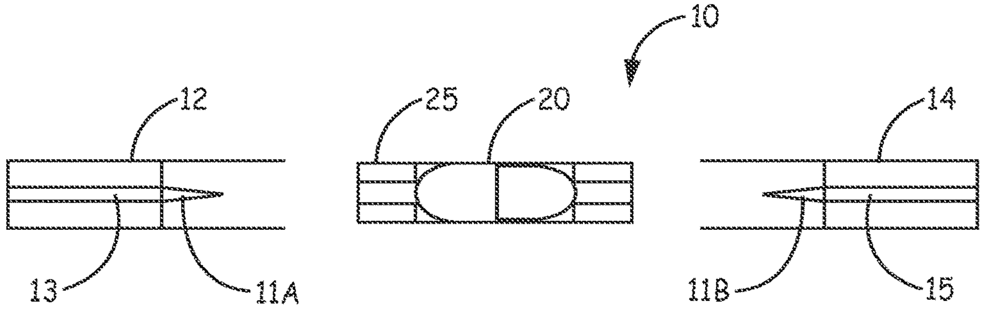

Referring now to FIG. 1 and FIG. 2, the nicotine powder inhalers 10 include a mouthpiece portion 12 and a distal end portion 14 and a nicotine capsule 20 disposed between them. Piercing elements 11A and 11B are configured to pierce the capsule 20 and fluidly connect the airflow channel 13 of the mouthpiece portion 12 with the airflow channel 15 of the distal end portion 14.

The airflow channel extends linearly along a length of the nicotine powder inhaler 10. FIG. 2 further illustrates the capsule 20 within a receptacle 25 that can be re-usable.

Figure 3:
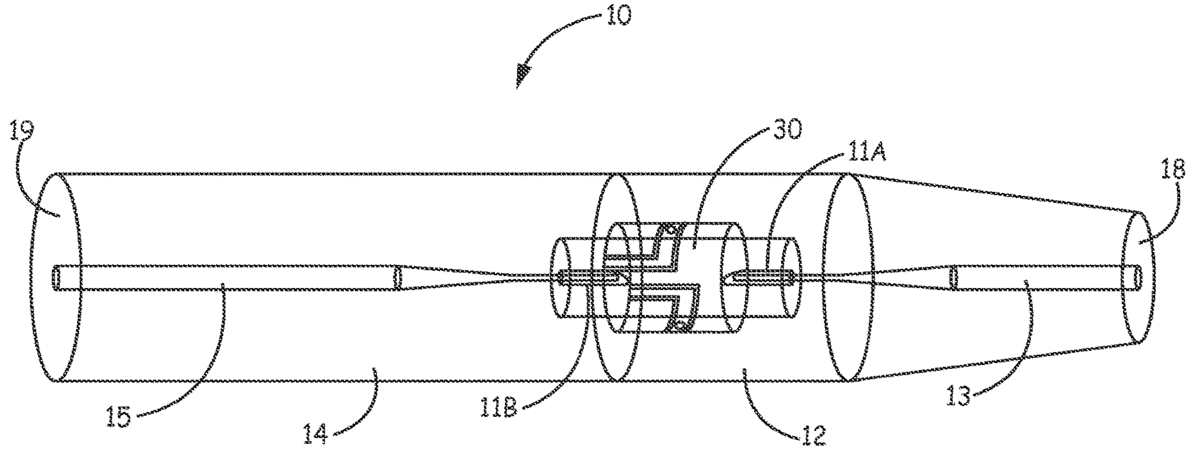
Figure 4:
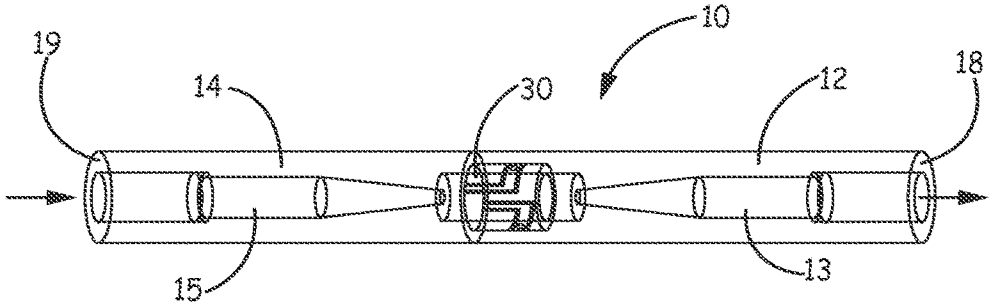

FIG. 3 and FIG. 4 illustrate nicotine powder inhalers 10 having a single linear airflow channel 13, 15. Piercing elements 11A and 11B extend into a nicotine powder receptacle 30 and are configured to pierce the nicotine powder capsule and fluidly connect the airflow channel 13 of the mouthpiece portion 12 with the airflow channel 15 of the distal end portion 14. The airflow channel extends linearly along a length of the nicotine powder inhaler 10 from a proximal mouthpiece end 18 to a distal end 19. The mouthpiece portion 12 can connect with the distal end portion 14 via a bayonet-type connection. In FIG. 3 the mouthpiece portion 12 is not symmetrical with the distal end portion 14. In In FIG. 4 the mouthpiece portion 12 is symmetrical with the distal end portion 14.

Figure 5:
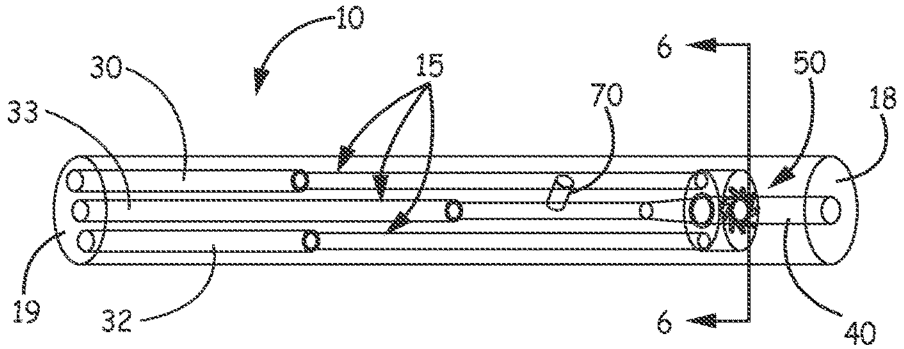
Figure 6:
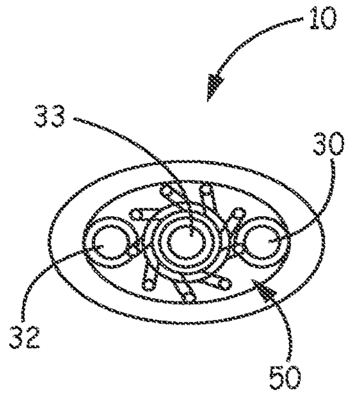

FIG. 5 and FIG. 6 is a further illustrative nicotine powder inhaler 10. FIG. 6 is a view of FIG. 5 taken along lines 6-6. This embodiment includes three airflow channels 15 and a first, second and third powder receptacles 30, 32 and 33 respectively. A nicotine powder capsule can be received in at least one of the powder receptacles 30, 32 and 33. In some embodiments, a second active agent can be received in at least one of the powder receptacles 30, 32 and 33.

The three flow channels 15 fluidly connect to an outlet channel 40 via a swirl generator 50 configured to induce rotation movement in the airflow. The airflow channels 15 extend linearly along a length of the nicotine powder inhaler 10 from a proximal mouthpiece end 18 to a distal end 19. A ventilation element 70 can be disposed along an airflow channels 15 to provide dilution air, as desired.

Figure 7:
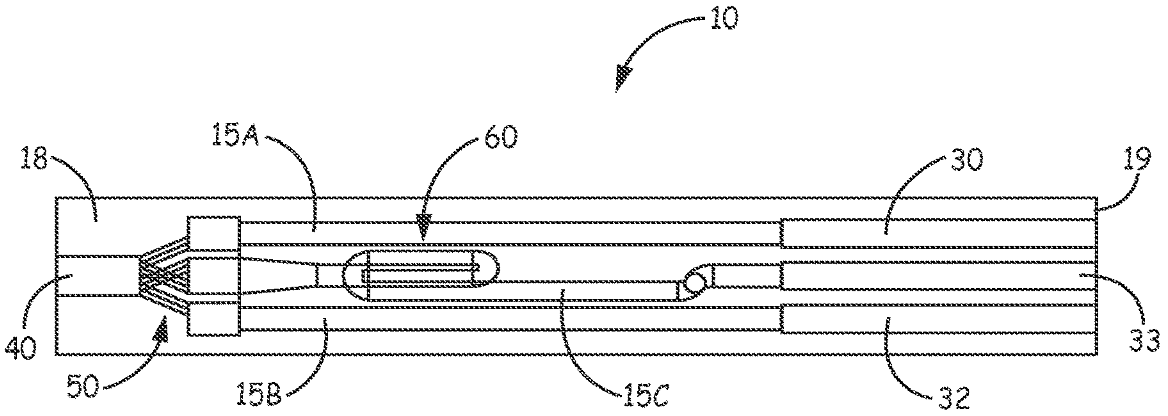

FIG. 7 is a further illustrative nicotine powder inhaler 10. This embodiment includes three airflow channels 15A, 15B and 15C and first, second and third powder receptacles 30, 32 and 33 respectively. A nicotine powder capsule can be received in at least one of the powder receptacles 30, 32 and 33. In some embodiments, a second active agent can be received in at least one of the powder receptacles 30, 32 and 33. The three flow channels 15 fluidly connect to an outlet channel 40 via a swirl generator 50 configured to induce rotation movement in the airflow. The airflow channels 15A, 15B extend linearly along a length of the nicotine powder inhaler 10 from a proximal mouthpiece end 18 to a distal end 19. In some embodiments an airflow loop element 60 is disposed along an airflow channels 15C.

The invention claimed is:

1. A powder inhaler comprising:

a body comprising a proximal mouthpiece portion and a distal end portion, the body extending along a longitudinal axis from a proximal mouthpiece end of the proximal mouthpiece portion to a distal end of the distal end portion, the distal end comprising an air inlet and the proximal mouthpiece end comprising an air outlet, the proximal mouthpiece portion being symmetrical with the distal end portion and the body having a uniform cylindrical shape from the distal end to the proximal end;

a swirl generator element disposed in the body and constructed to induce rotational movement in airflow moving through the body;

an airflow channel extending linearly along the body from the distal end to the proximal mouthpiece end;

a nicotine powder receptacle disposed along the airflow channel and separate from the swirl generator; and wherein the powder inhaler is constructed to deliver a dose of powder via airflow created by inhalation at the proximal mouthpiece end at an inhalation rate of less than about 3 L/min.

2. The powder inhaler according to claim 1, wherein the body is a linear extending from the distal end to the proximal mouthpiece end.

3. The powder inhaler according to claim 1, wherein the airflow channel is parallel with the longitudinal axis.

4. The powder inhaler according to claim 1, wherein the nicotine powder receptacle defines a cylindrical shape.

5. A system for providing powder, the system comprising the powder inhaler of claim 1 and further comprising a capsule containing nicotine powder, the capsule disposed within the receptacle.

6. The system of claim 5, wherein the capsule further comprises a flavourant powder.

7. The system of claim 5, wherein the capsule further comprises an active agent.

8. The system of claim 5, wherein the nicotine powder has a mean average particle size in a range from 1 micrometer to 7 micrometers.

9. The system of claim 8, wherein at least 90% of the nicotine powder has a particle size of 7 micrometers or less.

10. The system of claim 5, wherein the nicotine powder comprises L-Leucine.

11. The system of claim 5, wherein the nicotine powder comprises nicotine bitartrate.

12. The system of claim 5, wherein the nicotine powder comprises nicotine glutamate.

13. The system of claim 7, wherein nicotine powder comprises from 5 to 30 mg of nicotine powder to deliver a uniform dose of nicotine powder for each of at least 5 inhalations.

14. A method of inhaling powder into lungs of a user:

inhaling air through the system of claim 7 at a flow rate of less than about 2 L/min to deliver nicotine powder into lungs of a user.

15. The method of claim 14, wherein the inhaling air through the system induces rotational movement of air flowing through the powder inhaler.

16. The method of claim 14, wherein the inhaling air through the system induces rotational movement of air flowing through the powder inhaler and delivers nicotine powder and flavourant powder to a user.

* * * * *